United States Patent [19]

Howland

[11] Patent Number: 5,487,744
[45] Date of Patent: Jan. 30, 1996

[54] CLOSED CONNECTOR FOR SPINAL FIXATION SYSTEMS

[75] Inventor: Robert S. Howland, Seal Beach, Calif.

[73] Assignee: Advanced Spine Fixation Systems, Inc., Cypress, Calif.

[21] Appl. No.: 227,907

[22] Filed: Apr. 15, 1994

Related U.S. Application Data

[63] Continuation of Ser. No. 45,370, Apr. 8, 1993, abandoned.

[51] Int. Cl.$^6$ ............................................. A61B 17/70
[52] U.S. Cl. ............................................. 606/61
[58] Field of Search ..................... 606/60, 61, 62, 606/69, 73

[56] References Cited

U.S. PATENT DOCUMENTS

| | | | |
|---|---|---|---|
| 2,439,995 | 4/1948 | Thrailkill | 128/84 |
| 2,579,968 | 12/1951 | Rush | 606/62 |
| 4,483,334 | 11/1984 | Murray . | |
| 4,653,481 | 3/1987 | Howland et al. . | |
| 4,719,905 | 1/1988 | Steffee . | |
| 4,772,448 | 9/1988 | Popalis et al. | 376/463 |
| 4,773,402 | 9/1988 | Asher et al. | 606/61 |
| 5,000,165 | 3/1991 | Watanabe . | |
| 5,024,213 | 6/1991 | Asher et al. | 606/61 |
| 5,030,220 | 7/1991 | Howland | 606/73 |
| 5,053,034 | 10/1991 | Olerud | 606/61 |
| 5,085,660 | 2/1992 | Lin | 606/60 |
| 5,129,900 | 7/1992 | Asher et al. | 606/72 |
| 5,217,497 | 6/1993 | Mehdian | 623/17 |
| 5,290,288 | 3/1994 | Vignaud et al. | 606/61 |

FOREIGN PATENT DOCUMENTS

| | | |
|---|---|---|
| 283373 | 9/1988 | France . |
| 2615095 | 11/1988 | France . |
| 3032237 | 3/1982 | Germany . |
| 9111967 | 8/1991 | WIPO . |

OTHER PUBLICATIONS

Article, "Amset R–F Reduction–Fixation System Surgical Technique" in *AMS Innovation in Spine,* a training manual published by FIX Trauma Orthopaedics, 1991, pp. 1–19.
William L. Carson, Ph.D., "Biomechanical Overview of the Isola Modular Spine Implant System, An Introductionn", Sep. 16, 1989, Columbia, Missouri, pp. 1–26.
AcroMed Corporation, "Kanneda Anterior Spinal Instrumentation System Technique Manual", pp. 1–22.
DIMSO, "Spinal Fixation Diapason Device and Technique", pp. 1–5.
Sofamor Division Raquis, "Compact CD Los Back" Catalogo de los Productos, Brochure.

*Primary Examiner*—Tamara L. Graysay
*Attorney, Agent, or Firm*—Christie, Parker & Hale

[57] ABSTRACT

A spinal fixation device for immobilizing a portion of a spine includes at least one spine rod and a plurality of bone screws that are threaded into an appropriate number of vertebrae and each of which includes a threaded end protruding from the vertebra. Clamps are used to fasten a spine rod to the bone screws. Each clamp includes a body portion with a first aperture for receiving the protruding threaded end of a bone screw. The clamp is fastened to the threaded end of the bone screw with a nut. A second aperture receives the spine rod and includes a plurality of longitudinal teeth that cooperate with a serrated spine rod to provide a secure grip between the two and to prevent rotation of the spine rod with respect to the clamp. A threaded aperture communicates with the second aperture and receives a set screw for locking the rod within the second aperture.

16 Claims, 3 Drawing Sheets

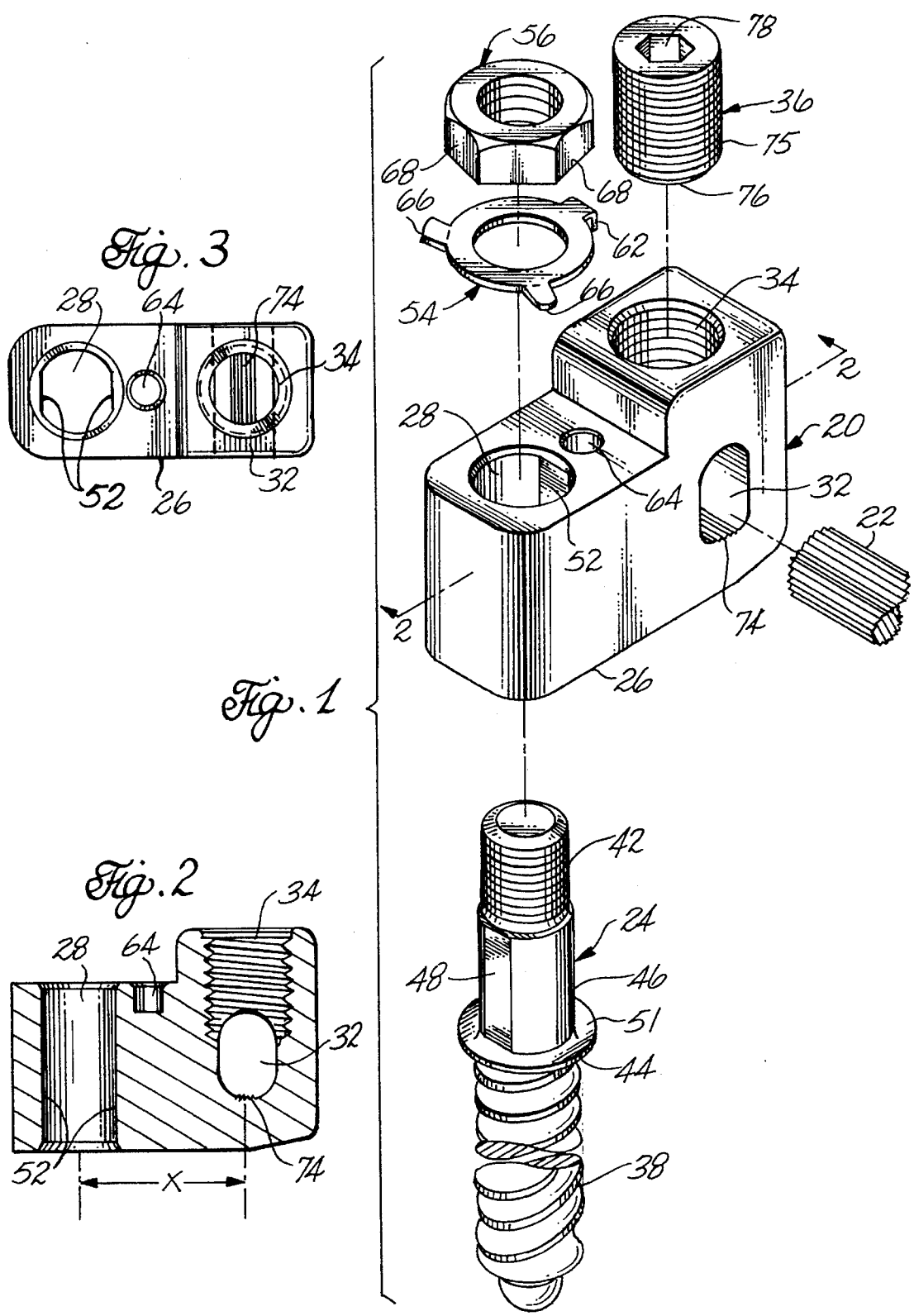

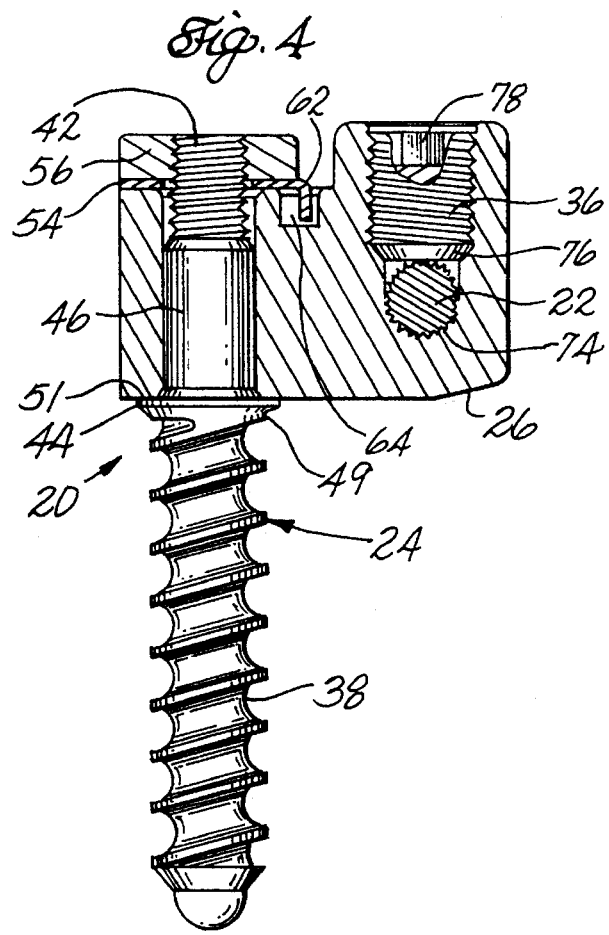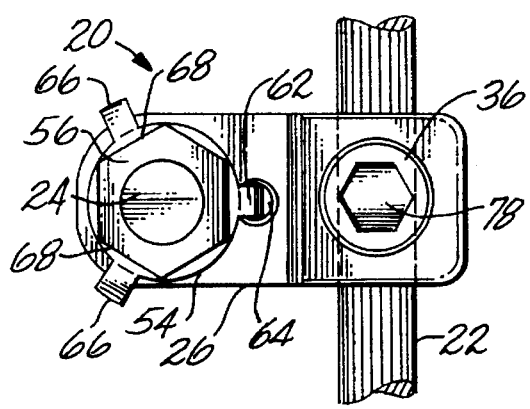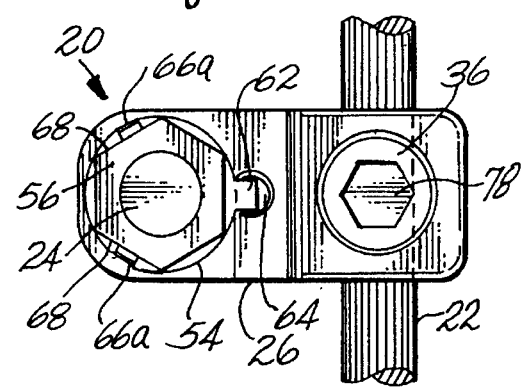

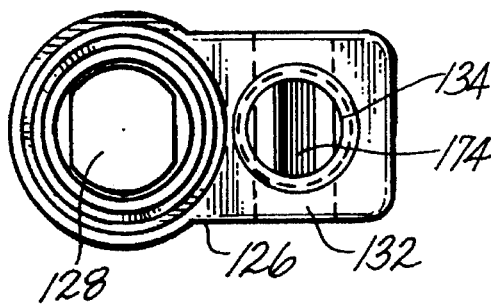
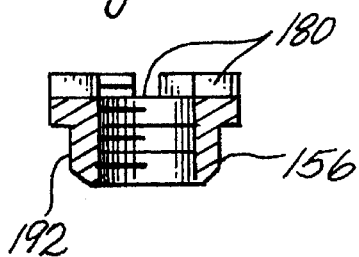
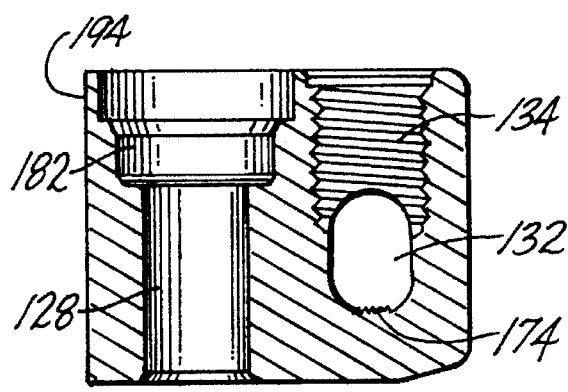
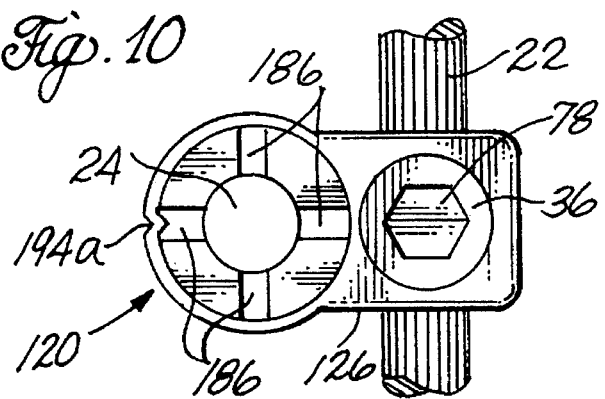

CLOSED CONNECTOR FOR SPINAL FIXATION SYSTEMS

CROSS-REFERENCE TO RELATED APPLICATION

This is a continuation of application Ser. No. 08/045,370, filed Apr. 8, 1993, now abandoned.

FIELD OF THE INVENTION

This invention relates to an implantable spinal fixation system for the surgical treatment of spinal disorders. More specifically, it relates to a closed connector for attaching a spine rod to a bone screw that is anchored in a vertebra.

BACKGROUND OF THE INVENTION

Various types of spinal column disorders are known and include scoliosis (abnormal lateral curvature of the spine), kyphosis (abnormal backward curvature of the spine), excess lordosis (abnormal forward curvature of the spine), spondylolisthesis (forward displacement of a lumbar vertebrae), and other disorders such as ruptured or slipped discs, broken or fractured vertebrae and the like. Patients who suffer from such conditions usually experience extreme and debilitating pain. A technique known as spinal fixation uses surgical implants which mechanically immobilize areas of the spine during surgical fusion of the treated vertebrae. Such techniques have been used effectively to treat such conditions and in most cases to bring the patient relief from pain.

One particular technique for spinal fixation includes the immobilization of the spine by the use of a pair of spine rods that run generally parallel to the spine. Bone screws are used as the anchor points for the spine rods and clamps are used to fasten the spine rods to the bone screws. Bone screws are generally placed two per vertebrae, one at each pedicle on either side of the spinous process with a protruding threaded end for anchoring the connector. Various different connectors have been developed for fastening a spine rod to a bone screw. Saddle clamps comprising a pair of mating half saddles that fit over the protruding threaded end of a bone screw and that are clamped together by a nut threaded to the bone screw are commonly used. Examples of such devices can be found in U.S. Pat. Nos. 4,653,481 and 5,030,220. These patents further disclose the use of spine rods and clamps that include longitudinal serrations which improve the grip between the spine rod and the clamps.

Other devices include a one-piece connector that has a first opening for receiving a spine rod and a second oblong opening for fastening the connector to a bone fastener with a threaded nut. A set screw can be threaded into a threaded aperture in communication with the first opening, to lock the rod in place. Such a connector is disclosed in U.S. Pat. No. 5,129,900.

Another clamp includes an articulating joint and is disclosed in U.S. Pat. No. 5,053,034. A first block is fastened to a bone screw and a second block with a protruding cylindrical arm fits into an aperture in the first block to form the articulating joint. The angle between the blocks can be adjusted by rotating the second block with respect to the first block at this joint. Once the desired angle is obtained, a set screw is threaded into a second aperture, in communication with the first aperture in the first block, to lock the two blocks together. A pair of such articulating joints are fastened to a pair of vertebrae and the two are fastened to each other by a "screw spindle" or other rigid connecting member.

There are several inadequacies with these devices. For example, the clamps often do not provide sufficient grip to prevent the spine rod from slipping with respect to the clamp. For some clamps, the clamp tends to slip with respect to the bone screw. This problem is especially apparent with laterally adjustable clamps. Furthermore, most of these devices are fairly bulky and portions of the clamp extend to high above the patient's spine which can lead to irritation of the patient's muscles and other tissue that rub against the clamp when it is installed. Moreover, some clamps tend to include several parts that must be assembled during surgery. Complicated assembly onto the spine increases the possibility that parts will be dropped or misplaced during surgery.

An improved one-piece clamp is desired that provides a strong and secure connection between a bone screw and a spine rod. Such a device should be easy to install and should include relatively few parts. It is also desirable that a one-piece clamp have a low profile so as to minimize irritation of the patient's surrounding muscles and other tissue.

SUMMARY OF THE INVENTION

A clamp for connecting a spine rod to a bone screw includes a body portion with a first aperture for receiving the threaded end of a bone screw that protrudes from a vertebra. A second aperture, which is available in incremental spacing from the first aperture is included in the body portion for receiving the spine rod and includes a plurality of longitudinal teeth for improving the grip between the clamp and the spine rod. The teeth are particularly effective at gripping a longitudinally serrated spine rod. A threaded aperture communicates with the second aperture and receives a set screw that provides the clamping force for holding the spine rod within the second aperture. The clamp is fastened to the bone screw by a nut threaded to the threaded end of the bone screw. The device preferably includes means for locking the nut to the clamp so that the device will not loosen once implanted.

At least two of such clamps can be used in combination with a spine rod to span a pair of vertebrae. More clamps can be used if a larger portion of the spine is to be immobilized. A pair of spine rods can also be used with pairs of clamps, each pair fastened to the two pedicles located on either side of each vertebra to be spanned.

BRIEF DESCRIPTION OF THE DRAWINGS

Features, aspects and advantages of the invention will be more fully understood when considered with respect to the following detailed description, appended claims and accompanying drawings where:

FIG. 1 is an isometric exploded view of the clamp along with a serrated spine rod and a bone screw;

FIG. 2 is an elevation view, in section, of the body portion of a clamp taken along line 2—2 of FIG. 1 showing the "X" dimension which is made in incremental spacing;

FIG. 3 is a top view of the body portion of FIG. 1;

FIG. 4 is an elevation view, partly in section, of an assembled clamp;

FIGS. 5 and 6 are top views of an assembled clamp showing the lock washer before and after it has been locked in place;

FIG. 7 is an elevation view, in section, of the body portion of a low profile clamp design;

FIG. 8 is a top view of the body portion of FIG. 7;

FIG. 9 is an elevation view in section of a sleeve nut for use with the low profile body portion of FIG. 7; and FIG. 10 is a top view of a low profile clamp with the sleeve nut locked in place.

DETAILED DESCRIPTION

The present invention relates to clamps for use in connecting spine rods to bone screws after their placement in the various vertebrae of a spinal column. Such clamps are part of a spinal fixation system that is useful for correcting various abnormal spine conditions. These systems are surgically implanted to immobilize at least a portion of a patient's spine. In performing the surgery, a surgeon first exposes the patient's spine. Holes are tapped in the pedicles of appropriate vertebrae and bone screws are threaded into place. A spine rod is bent to an appropriate curvature and clamps are used to fasten the rod to the bone screws causing the immobilization of a portion of the spine.

While the clamping device of this invention will generally be described for use with bone screws, it is clear that it could also be used to connect other vertebra fasteners to a spine rod. Other vertebra fasteners that might be used are lamina hooks. Any such vertebra fastener can be used in conjunction with the clamps of this invention so long as it includes a portion that extends outwardly from the spine that can be fastened to the clamp.

Referring to FIG. 1, a clamp 20 is shown for fastening a serrated spine rod 22 to a bone screw 24. The clamp includes a generally L-shaped body portion 26 that includes a first aperture 28 for receiving the bone screw, a second aperture 32 for receiving the spine rod and a threaded aperture 34 for receiving a set screw 36 which locks the spine rod within the second aperture. Details of body portion 26 are shown in FIGS. 2, 3 and 4.

The apertures are arranged so that the second aperture which receives the spine rod is found in a plane that is generally perpendicular to the first aperture which receives the bone screw. This is the proper orientation as bone screws are generally placed perpendicular to the spine, especially in the vertebrae located in the mid to lower region of the spine. This provides proper placement of the spine rod which generally runs parallel to the spine. If clamps are to be placed in the upper portions of the spine, especially in the cervical region, the plane containing the second aperture should be offset from perpendicular to the bone screw to account for different bone screw placement dictated by physiological differences of the upper vertebrae compared to the lower vertebrae.

The threaded aperture is in communication with the second aperture and is preferably oriented perpendicular to the second aperture so that the set screw can tightly secure the spine rod within the clamp. In order to provide optimum access for assembling the spinal fixation device during surgery, the threaded aperture should face outwardly from the patient's spine. The set screw is placed completely within the threaded aperture without any part protruding so as to provide a low profile and minimize irritation of the patient's surrounding muscles and other tissue.

Bone screws for use with such a clamp are generally well known. Referring to FIG. 1, bone screw 24 includes a first threaded end 38 which generally has a coarse thread for anchoring the bone screw within a hole tapped in a vertebra. At an end opposite the first threaded end is a second threaded end 42 with a more fine thread that is used to fasten the bone screw to the clamp. Between the two threaded ends is a flange 44 having a tapered side 49 that rests against the surface of a vertebra when the bone screw is in place. Opposite the tapered side is a flat side 51 upon which the clamp rests. Such a flange improves the strength of a spinal fixation system by preventing the clamp from contacting the surface of the vertebra. If the clamp were allowed to directly contact the vertebra, any force that is applied to the spinal fixation system results in a lever action that tends to dislodge the bone screw from the vertebra.

Between the flange and the second threaded end is a generally cylindrical section 46 for receiving the clamp 20. The generally cylindrical section includes longitudinally extending external flats 48 which cooperate with similar internal flats 52 in the first aperture of the body portion of the clamp. The internal flats are best shown in FIG. 3. The external flats of the bone screw and the internal flats of the clamp prevent the clamp from rotating with respect to the bone screw once the clamp is assembled onto the bone screw.

While a generally cylindrical section with flats is described, it is clear that other shapes would adequately perform the same function. For example, a screw with a portion having a square or other polygonal cross section would work well with a similarly shaped first aperture to prevent the clamp from rotating with respect to the bone screw.

Once the clamp has been placed over the bone screw it is fastened in place by lock washer 54 and hexagonal threaded nut 56. The lock washer is used to prevent the nut from rotating with respect to the clamp and loosening once the clamp has been fastened to the bone screw.

A plurality of tabs extend radially from the washer. A lower tab 62 extends first outwardly and then downwardly toward the body portion of the clamp and cooperates with a notch 64 defined by the body portion. When located in the notch this lower tab prevents the washer from rotating with respect to the body portion. A pair of deformable tabs 66 can be bent up, toward the nut, to interfere with two faces 68 of the nut once the nut has been properly tightened.

The operation of the lock washer is illustrated in FIGS. 5 and 6, top views of the clamp. The lower tab 62 is shown placed into notch 64 of the clamp and the nut 56 is tightened to the second threaded end 42 of the bone screw. In FIG. 5, deformable tabs 66 of the lock washer are shown before they have been bent up to interfere with faces 68 of the nut. Once the nut has been properly tightened, tabs 66 are bent upwardly as illustrated as tabs 66a in FIG. 6, preventing the nut from rotating with respect to the body portion of the clamp. Of course, if readjustment is necessary, the tabs can be bent down to allow the nut to be loosened.

Spine rod 22 fits into second aperture 32 of the clamp. The second aperture is an oval cross-sectional shaped aperture. The major axis of the oval runs generally parallel to the longitudinal axis of the threaded aperture. This simplifies insertion of the rod into the second aperture by affording some up and down play between the clamp and the spine rod during assembly while still allowing the set screw to firmly hold the rod in place once proper orientation has been achieved.

The second aperture also includes a plurality of longitudinal teeth 74 opposite the threaded aperture which cooperate with serrations on a spine rod to improve the grip between the clamp and spine rod. The grip is improved because the teeth interlock with the serrations to prevent rotation of the rod with respect to the clamp when the two are fastened together. The grip is further improved because the teeth and serrations cooperate to increase the amount of surface area in contact between the clamp and the spine rod to increase the friction between the two.

Set screw 36 is used to lock the rod in place within the second aperture. The set screw has a thread 75 along its length, a tip 76 at a first end and a keyed opening 78 at a second end opposite the tip. The set screw is threaded into threaded aperture 34 which runs perpendicular to and is in communication with the second aperture. The tip of the set screw engages with the spine rod, pressing it against the teeth to lock the rod in place. The keyed opening allows the set screw to be driven into the threaded aperture with the use of a suitable tool such as a hex key.

An assembled clamp of a preferred embodiment of the invention is illustrated in section in FIG. 4. One of the primary benefits of the invention is that it has a fairly low profile, that is, it does not extend very far away from the spine when installed. Furthermore, as is shown in FIG. 4, the top of the assembled clamp is fairly flat and has no protruding portions. The nut 56 that holds the clamp to the bone screw 24 is basically flush with the top of the threaded aperture. This low profile and flat design reduces the potential for irritation of the patient's muscles. Complications are often associated with higher profile clamps and clamps with protruding portions.

In assembling a spinal fixation system that uses the clamps of this invention, the first step after exposing the patient's spine is to position an appropriate number of bone screws in the pedicles of the vertebrae along the portion of the spine to be immobilized. Once the bone screws are in place, a spine rod is cut to length and bent appropriately to achieve the desired curvature of the spine. Clamps with selected aperture spacing are placed along the spine rod and placed over the bone screws. At this point it may be desirable to "fine-tune" the bending of the rod as necessary. Lock washers and nuts are then placed over the second threaded portion of each of the bone screws taking care to place each lock washer so that lower tab 62 engages with notch 64 in the body portion of the clamp. The nuts are then tightened to firmly hold each clamp to its respective bone screw. Set screws are threaded into the threaded apertures of the body portions and tightened to lock the spine rod within the second apertures. The final step is then to bend the deformable tabs of the lock washers upward to engage faces of the nuts.

In order to reduce the number of small parts that must be handled during surgery it is preferred that some preassembly take place before the surgery begins. For example, set screw 36 can be threaded loosely into the threaded aperture of the body portion of the clamp while still allowing simple placement of the rod within the second aperture. It is also preferred that the lock washer be preassembled to the body portion. This is achieved by placing the lock washer 54 over the body portion 26 and pressing lower tab 62 of the lock washer into notch 64 of the body portion. An interference fit between the lower tab and the notch holds the lock washer to the body portion.

It is also desirable that the deformable tabs 66 of the lock washer be bent upward slightly before assembly so as to make them easier to grip for final bending when the nut is tightly in place. However, it should be noted that such pre-bending should be slight so as to prevent interference with the faces of the nut as it is tightened into place. It should also be recognized that the outer surfaces of the parts should generally be rounded, as is shown in FIGS. 1–7, so as to minimize irritation of sensitive body tissue once the device has been implanted.

In a preferred embodiment of the present invention, the body portion of the clamp is manufactured in different sizes where aperture spacing length X (FIG. 2) between the center lines of the first and second apertures varies. An assortment of various sized clamps allows a custom fit for each application. By carefully selecting a clamp of an appropriate size, bending of the rod can be reduced. This can shorten the surgery time reducing possible complications associated with lengthy surgical procedures and can result in a stronger construct. Numerous sharp bends in a spine rod can tend to weaken a rod. The use of various sized clamps is preferred over adjustable clamps as they provide a more rigid construct that is less likely to later loosen or shift. The aperture spacing length X varies between about 6 mm and 12 mm in increments of about 1 mm for a preferred assortment of clamps.

In another embodiment of the present invention, the clamp comprises an even lower profile shape which further reduces the possibility of irritation of body tissue. In this embodiment, the nut that holds the clamp to the bone screw is recessed within the body portion of the clamp. This configuration has the same basic configuration as the previously described clamp but offers an even lower profile. FIGS. 7 through 10 illustrate such a low profile clamp 120 and its components.

In FIGS. 7 and 8, a generally rectangular shaped body portion 126 includes a first aperture 128 for receiving the second threaded end of the bone screw (not shown) which is the same as that described previously. A second aperture 132 receives the spine rod and includes a plurality of teeth 174 for improving the grip between the clamp and the spine rod. Threaded aperture 134 receives a set screw (not shown) as described previously for locking the rod within the body portion. The arrangement of these three apertures is generally the same as that described previously.

The upper portion of the first aperture of the body portion of the low profile clamp further includes a circular stepped recess 182 for receiving a sleeve nut 156 as shown in sectional view on FIG. 9. The sleeve nut is shown in place on a clamp in FIG. 10. The sleeve nut includes four radially arranged slots 186 in its upper portion which allow it to be driven into place with a suitable pronged tool (not shown). The external surface 192 of the sleeve nut is stepped to cooperate with the stepped recess. The steps of the recess and the sleeve nut work together to distribute the clamping force along a larger surface of the clamp, and therefore, improve its grip to the bone screw. It is the use of this sleeve nut that allows the nut to be completely located within the body portion of the clamp providing the clamp with a particularly low profile design.

The stepped recess of the body portion of the low profile clamp further defines a thin, deformable wall 194 at the top of the body portion which can be used to lock the sleeve nut in place once it has been tightened to the bone screw. The sleeve nut is locked by placing a crimp 194a, as shown in FIG. 10, in the wall after the nut has been tightened. This crimp interferes with one of the slots in the sleeve nut so that the nut is prevented from rotating with respect to the body portion of the clamp. Of course, if the sleeve nut needs to be removed, the same pronged driving tool that was used to tighten the sleeve nut can be used to engage the slots and provide sufficient torque to remove the crimp in the wall.

The components of the clamp of the present invention are preferably made of an alloy capable of resisting corrosion when installed in a human body. It has been found that 316 stainless steel which has been electro-polished and passivated to resist corrosion works well. Other metal alloys such as alloys of titanium also work well.

The present invention is not to be limited to the specific designs shown which are merely illustrative. Various and numerous other arrangements may be devised by one skilled in the art without departing from the spirit and scope of this invention. The scope of the invention is defined in the following claims.

What is claimed is:

1. A clamp assembly for connecting a spine rod to a vertebra fasteners, the clamp assembly comprising:

a spine rod;

a vertebra fastener including a shaft having a first threaded end for insertion into a vertebra and a second threaded end for receiving a threaded nut;

an L-shaped clamp having a body portion forming one side of the L-shape and a foot portion forming the foot of the L-shape comprising:

a first outward, away-from-the-spine surface forming one side of the body portion of the L-shape;

a first aperture for receiving the shaft of the vertebra fastener with an opening of the first aperture in the first outward, away-from-the-spine surface;

a second aperture for receiving the spine rod and cooperating with the spine rod to securely grip the rod to the body portion;

a second outward, away-from-the-spine surface forming one end of the foot portion of the L-shape, having surface plane which is not co-planar with the first outward, away-from-the-spine surface; and a threaded aperture, with an opening of the threaded aperture in the second outward, away-from-the-spine surface, in communication with the second aperture;

a set screw for threading into the threaded aperture to clamp the spine rod within the second aperture;

a threaded nut having an upper surface and a lower surface for fastening the body portion to the second threaded portion of the vertebra fastener wherein when the nut is threaded to the vertebra fastener and the lower surface rests on the first outward, away-from-the-spine surface, the upper surface is substantially coplanar with the second outward away-from-the-spine surface so that the assembled clamp has a generally flat planar profile outward, away from the spine, without any portions substantially protruding from the clamp outwardly, away from the spine, thereby inhibiting irritation to the back muscles of a patient once the system is installed; and means for locking the nut to the body portion to prevent the nut from loosening.

2. The clamp assembly of claim 1 wherein the locking means comprises a washer with at least one lower tab for cooperating with a notch in the body portion and at least one deformable tab for cooperating with the threaded nut.

3. A clamp assembly for connecting a spine rod to a vertebra fastener, the clamp assembly comprising:

a spine rod;

a vertebra fastener including a shaft having a first threaded end for insertion into a vertebra and a second threaded end for receiving a threaded nut;

an L-shaped clamp having a body portion forming one side of the L-shape and a foot portion forming the foot of the L-shape comprising:

a first outward, away-from-the-spine surface forming one side of the body portion of the L-shape;

a first aperture for receiving the shaft of the vertebra fastener with an opening of the first aperture in the first outward, away-from-the-spine surface;

a second aperture for receiving the spine rod and cooperating with the spine rod to securely grip the rod to the body portion;

a second outward, away-from-the-spine surface forming one end of the foot portion of the L-shape, having a surface plane which is not co-planar with the first outward, away-from-the-spine surface; and a threaded aperture, with an opening of the threaded aperture in the second outward, away-from-the-spine surface, in communication with the second aperture;

a set screw for threading into the threaded aperture to clamp the spine rod within the second aperture;

a threaded nut having an upper surface and a lower surface for fastening the body portion to the second threaded portion of the vertebra fastener wherein when the nut is threaded to the vertebra fastener and the lower surface rests on the first outward, away-from-the-spine surface, the upper surface is substantially co-planar with the second outward away-from-the-spine surface so that the assembled clamp has a generally flat planar profile outward, away from the spine, without any portions substantially protruding from the clamp outwardly, away from the spine, thereby inhibiting irritation to the back muscles of a patient once the system is installed; and means for preventing rotation of the clamp about an axis longitudinal to the bone screw.

4. The clamp assembly of claim 3 wherein the means for preventing rotation comprises at least one longitudinal internal flat in the first aperture that cooperates with at least one longitudinal external flat on the shaft of the vertebra fastener.

5. A clamp assembly for connecting a spine rod to a vertebra fastener, the clamp assembly comprising:

a spine rod;

a vertebra fastener including a shaft having a first threaded end for insertion into a vertebra and a second threaded end for receiving a threaded nut;

an assortment of L-shaped clamps having a body portion forming one side of the L-shape and a foot portion forming the foot of the L-shape comprising:

a first outward, away-from-the-spine surface forming one side of the body portion of the L-shape;

a first aperture for receiving the shaft of the vertebra fastener with an opening of the first aperture in the first outward, away-from-the-spine surface;

a second aperture for receiving the spine rod and cooperating with the spine rod to securely grip the rod to the body portion;

a second outward, away-from-the-spine surface forming one end of the foot portion of the L-shape, having a surface plane which is not co-planar with the first outward, away-from-the-spine surface; and a threaded aperture, with an opening of the threaded aperture in the second outward, away-from-the-spine surface, in communication with the second aperture;

a set screw for threading into the threaded aperture to clamp the spine rod within the second aperture;

a threaded nut having an upper surface and a lower surface for fastening the body portion to the second threaded portion of the vertebra fastener wherein when the nut is threaded to the vertebra fastener and the lower surface rests on the first outward, away-from-the-spine surface, the upper surface is substantially co-planar with the second outward away-from-the-spine surface so that the assembled clamp has a generally flat planar profile outward, away from the spine, without any portions substantially protruding from the clamp outwardly, away from the spine, thereby inhibiting irritation to the back muscles of a patient once the system is installed; and wherein the clamps in the assortment have various aperture spacing lengths.

6. The assortment of clamps of claim 5 wherein the aperture spacing lengths are between about 6 mm and about 12 mm.

7. The assortment of clamps of claim 6 wherein the clamps have aperture spacing lengths that vary from one another in increments of about 1 mm.

8. The assortment of clamps of claim 5 wherein the spine rod further comprises a plurality of serrations longitudinal to the spine rod and wherein the second aperture further comprises a plurality of teeth for cooperating with the serrations of the spine rod.

9. A clamp assembly for connecting a spine rod to a vertebra fastener, the clamp assembly comprising:

a vertebra fastener comprising a shaft having a threaded first end for fastening the vertebra fastener to a vertebra and a threaded second end for fastening a clamp to the vertebra fastener;

a threaded nut;

a clamp comprising:

a body;

a first aperture within the clamp body for receiving the second threaded end of the vertebra fastener, the first aperture further comprising a recess corresponding to the shape of the threaded nut wherein when the nut is threaded onto the vertebra fastener to fasten the clamp body to the vertebra fastener, the nut is completely countersunk into the clamp body such that the clamp has a generally flat planar profile without any portion of the threaded nut substantially protruding from the clamp body;

a second aperture within the clamp body for receiving the spine rod and cooperating with the spine rod to securely grip the rod to the clamp body; and a threaded aperture within the clamp body in communication with the second aperture; and a set screw for threading into the threaded aperture for clamping the spine rod within the second aperture.

10. The clamp assembly of claim 9 wherein the clamp body further comprises a wall adjacent the nut, whereby the nut can be prevented from rotating with respect to the clamp body by placing a crimp in the wall for interfering with at least one of four radially arranged slot surface element of the nut, wherein the wall is sufficiently thin so that the crimp can be made with a hand tool.

11. The clamp assembly of claim 9 further comprising means for preventing rotation of the clamp about an axis longitudinal to the vertebra fastener.

12. The clamp assembly of claim 11 wherein the means for preventing rotation comprises at least one longitudinal internal flat in the first aperture that cooperates with at least one longitudinal external flat on the shaft of the vertebra fastener.

13. The clamp assembly of claim 9 further comprising an assortment of clamps wherein the clamps in the assortment have various aperture spacing lengths.

14. The assortment of clamps of claim 13 wherein the aperture spacing lengths are between about 6 mm and about 12 mm.

15. The assortment of clamps of claim 14 wherein the clamps have aperture spacing lengths that vary from one another in increments of about 1 mm.

16. The clamp assembly of claim 9 wherein the spine rod further comprises a plurality of serrations longitudinal to the spine rod and wherein the second aperture of the clamp further comprises a plurality of teeth for cooperating with the serrations of the spine rod.

* * * * *